(12) United States Patent
Chaiken et al.

(10) Patent No.: US 6,389,306 B1
(45) Date of Patent: May 14, 2002

(54) METHOD FOR DETERMINING LIPID AND PROTEIN CONTENT OF TISSUE

(75) Inventors: Joseph Chaiken, Fayetteville, NY (US); Charles M. Peterson, Potomac, MD (US)

(73) Assignee: LighTouch Medical, Inc., New Hope, PA (US)

( * ) Notice: Subject to any disclaimer, the term of this patent is extended or adjusted under 35 U.S.C. 154(b) by 0 days.

(21) Appl. No.: 09/420,867

(22) Filed: Oct. 19, 1999

Related U.S. Application Data

(63) Continuation-in-part of application No. 09/295,975, filed on Apr. 21, 1999, now Pat. No. 6,292,686.
(60) Provisional application No. 60/083,039, filed on Apr. 24, 1998.

(51) Int. Cl.[7] ................................................ A61B 6/00
(52) U.S. Cl. ..................................... 600/474; 356/301
(58) Field of Search ................................ 600/407, 310, 600/322, 476, 477, 473, 475; 356/301, 302, 318

(56) References Cited

U.S. PATENT DOCUMENTS

| | | | |
|---|---|---|---|
| 5,159,929 A | | 11/1992 | Morris et al. |
| 5,372,135 A | | 12/1994 | Mendelson et al. |
| 5,553,616 A | * | 9/1996 | Ham et al. .................. 600/316 |
| 5,631,141 A | * | 5/1997 | Sonek et al. .................. 435/29 |
| 5,991,653 A | * | 11/1999 | Richards-Kortum et al. .................. 600/475 |
| 6,002,476 A | * | 12/1999 | Treado ........................ 356/301 |
| 6,040,906 A | * | 3/2000 | Harhay ........................ 356/301 |
| 6,095,982 A | * | 8/2000 | Richards-Kortum et al. .................. 600/476 |
| 6,160,617 A | * | 12/2000 | Yang ........................... 356/300 |
| 6,205,354 B1 | * | 3/2001 | Gellermann et al. ........ 600/477 |
| 6,208,887 B1 | * | 3/2001 | Clarke ......................... 600/476 |
| 6,289,230 B1 | * | 9/2001 | Chaiken et al. ............. 600/322 |
| 6,292,686 B1 | * | 9/2001 | Chaiken et al. ............. 600/476 |

FOREIGN PATENT DOCUMENTS

| | | |
|---|---|---|
| EP | 0 247 777 | 12/1987 |
| WO | WO 93/00856 | 1/1993 |
| WO | WO 96/03074 | 2/1996 |
| WO | WO 97/36540 | 10/1997 |
| WO | WO 98/03847 | 1/1998 |

OTHER PUBLICATIONS

H.G.M. Edwards et al. (1996) Chemistry in Australia pp. 454–455.
H.G.M. Edwards et al. (1995) Journal of Molecular Structure 347:379–388.
E.E. Lawson et al. (1997) Journal of Raman Spectroscopy 28:111–117.
A.T. Tu (1982) Raman Spectroscopy in Biology, John Wiley & Sons, NY.
K.G. Brown et al. (1973) Biochem. Biophys. Res. Commun. 54:358–364.
K. Larsson (1973) Chem. Phys. Lipids 10:165–176.
R. Mendelsohn (1973) Nature 243:22–24.

* cited by examiner

*Primary Examiner*—Marvin M. Lateef
*Assistant Examiner*—Shawna J Shaw
(74) *Attorney, Agent, or Firm*—Gates & Cooper LLP

(57) ABSTRACT

Disclosed is a method of modulating temperature of tissue in a subject to be spectroscopically probed. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue. The invention also provides a method for determining phase transition, and a method for determining lipid content and identity and protein content and identity in a tissue of a subject.

18 Claims, 12 Drawing Sheets

METHOD FOR DETERMINING LIPID AND PROTEIN CONTENT OF TISSUE

This application is a continuation-in-part of U.S. patent application Ser. No. 09/295,975, filed on Apr. 21, 1999, now U.S. Pat. No. 6,292,686, issued on Sep. 18, 2001, which application claims the benefit of United States provisional patent application Ser. No. 60/083,039, filed on Apr. 24, 1998, the entire contents of which are hereby incorporated by reference into this application. Throughout this application various publications are referenced. The disclosures of these publications in their entireties are hereby incorporated by reference into this application in order to describe more fully the state of the art to which this invention pertains.

TECHNICAL FIELD OF INVENTION

The invention relates to a method for determining tissue content, such as lipid and protein content, in a tissue of a subject. The method involves modulating the temperature of the tissue being analyzed and collecting spectra emitted under differing temperature conditions.

BACKGROUND OF THE INVENTION

There has long been considerable interest in the noninvasive monitoring of body chemistry and a need for reliable and precise quantitative methods for diagnosing medical abnormalities and for assessing the general condition of body tissues. While any approach that offers early and reliable warning of medical problems has some utility, noninvasive methods offer many advantages. Anticipation by a patient of pain and scarring associated with invasive procedures can cause delays in seeking medical attention. There is also a myriad of inconveniences, risks and difficulties associated with direct collection and contact with patient body fluids. For these reasons, there has been intense scientific and engineering research into devising noninvasive approaches to assessment and diagnosis of medical conditions.

Use of spectroscopic methods, while of considerable use in direct in vitro application to fluids, has not found equal in vivo application. In vivo sampling is substantially more complicated for a variety of reasons, although some of the challenges can be handled by reference to in vitro procedures. First, even in vitro procedures require at least some sample preparation before spectroscopic interrogation. But in vivo samples cannot be handled with nearly the ease of in vitro samples. All chemometric analyses benefit from the availability of samples having known composition of various analytes. Selectively modulated in vitro samples are much easier to synthesize or otherwise obtain than in vivo samples. Thus, samples for chemometric interpretation of in vivo samples can be expected to require specialized approaches to sample preparation and specifically designed methods for obtaining modulated samples of known composition. Long data collection times are needed to extract small signals from some samples, but in vivo sampling requires the patient to endure the waiting. Prolonged data collection is not always practical. Moreover, applying too much excitation light to in vivo samples can lead to catastrophic results.

Noninvasive in vivo chemical analysis of human and animal tissues has long been a goal of chemists and the medical community. Blood oximetry is an example of a noninvasive form of analysis that is now ubiquitous in intensive care and other situations. Noninvasive techniques involve contacting the tissue in question with some form of electromagnetic radiation, and detecting the effect of the contact on the radiation. The frequency range of the radiation and the choice of tissue to contact, determines the type of structural, concentration or other physico-chemical information available. Optimal application of noninvasive techniques for tissue analysis will require improved methods for isolating signals attributable to particular elements within tissues.

SUMMARY OF THE INVENTION

To overcome the limitations of the prior art, the invention provides a method for monitoring phase transitions, and thereby methods for determining lipid and protein content and identity in a tissue of a subject. The method can be performed in vivo and noninvasively. The method is preferably used with noninvasive spectroscopy, such as Raman spectroscopy, for the analysis of various features of tissue in a subject.

In one embodiment, the invention provides a method of determining lipid content of tissue in a subject. The method comprises contacting the tissue with electromagnetic radiation having an excitation wavelength, collecting the Raman spectra emitted by the tissue in a range of wavelengths associated with lipids, and altering the temperature of the tissue. Examples of a range of wavelengths associated with lipids include, but are not limited to, about 1450–1500 $cm^{-1}$ or about 2850–2890 $cm^{-1}$. The method further comprises repeating the contacting and collecting steps while the temperature of the tissue is altered, and analyzing the spectra collected to determine an amount of lipid present in the tissue. Preferably, the temperature of the tissue is altered by cooling. For example, the tissue can be cooled to about 1° C. to about 35° C. Preferably, the tissue is cooled to about 2° C. to about 12° C. In one embodiment, the analyzing comprises determining the difference in number of Raman shifted photons emitted by the tissue in the differing temperature conditions. Preferably, the tissue is a fingertip.

In another embodiment, the invention provides a method of determining protein content of tissue in a subject. The method comprises contacting the tissue with electromagnetic radiation having an excitation wavelength, collecting the Raman spectra emitted by the tissue in a range of wavelengths associated with protein, and altering the temperature of the tissue. Examples of a range of wavelengths associated with protein include, but are not limited to, about 1610–1700 $cm^{-1}$. The method further comprises repeating the contacting and collecting steps while the temperature of the tissue is altered, and analyzing the spectra collected to determine an amount of protein present in the tissue. Preferably, the temperature of the tissue is altered by cooling. For example, the tissue can be cooled by about 2 to about 35° C. In one embodiment, the analyzing comprises determining the difference in number of Raman shifted photons emitted by the tissue in the differing temperature conditions. Preferably, the tissue is a fingertip.

In one embodiment, the method further comprises determining the depth of a source of the spectra emitted by the tissue. For example, the determining can comprise using a confocal lens system to collect emitted spectra. The analyzing can further comprise determining the type of lipid or protein present in the tissue based on the depth of the source of the spectra emitted by the tissue.

In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue. The collected spectra are then analyzed to determine the lipid content, lipid identity and/or protein content and identity of the tissue. Preferably, the analysis comprises determining the difference in number of Raman shifted photons emitted by the tissue at different temperatures.

DETAILED DESCRIPTION

Figures 1, 2:
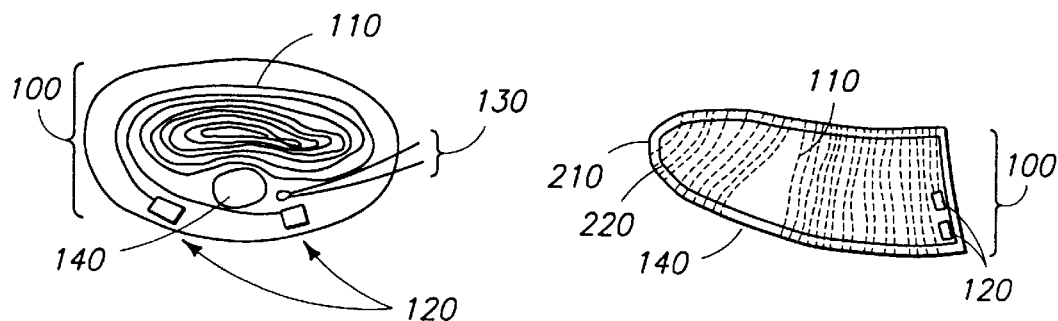
FIG. 1 is a front view of a tissue modulation device adapted to fit a fingertip.
FIG. 2 is a side view of the tissue modulation device shown in FIG. 1.

The invention disclosed herein describes an apparatus for the manipulation of temperature in tissue modulation. The apparatus can be used noninvasively. The apparatus provides control of the tissue temperature during modulation. The apparatus modulates tissue properties as well as blood flow and content using either thermally induced vasodilatation and vasoconstriction, or thermally induced lipid-based order-disorder transitions or protein unfolding dynamics. When tissue temperature is lowered, blood flow to and from the region of tissue is diminished. When tissue temperature is raised, blood flow returns to the affected tissue. Manipulation of flow and temperature allows more complete modulation of blood and fluid content. The difference between measurements taken in the blood replete and blood depleted states provides a measure indicative of components in the blood while minimizing the effects of extraneous spectroscopic signals due to calluses, oils, dirt, soap residue and other sources associated with the surrounding tissue. When thermal tissue modulation is employed during noninvasive spectroscopy, for example, the analysis can include determining the difference between the spectra collected in the blood replete and the blood depleted states. The method can also involve inducing changes in protein folding and lipid states of aggregation. These changes can be used to determine lipid identity and content or protein identity and content in blood and surrounding tissues. The methods can also be used to determine analyte concentrations, such as glucose, urea, triglycerides, creatinine, lactate, pyruvate, and others.

Definitions

All scientific and technical terms used in this application have meanings commonly used in the art unless otherwise specified. As used in this application, the following words or phrases have the meanings specified.

As used herein, "tissue" means any portion of an organ or system of the body, including, but not limited to, skin, capillary beds, blood, muscle, breast and brain. Preferably, the tissue is blood in capillary beds of a fingertip.

As used herein, "blood replete" refers to a state in which blood flow through and interstitial fluid content of a tissue is unobstructed by, for example, vasoconstriction induced by cooling or the application of pressure. The blood replete state can be enhanced by conditions which increase vasodilatation, such as warming.

As used herein, "blood depleted" refers to a state in which blood flow through and interstitial fluid content of a tissue is substantially restricted and blood volume is minimized. A blood depleted state can be achieved by, for example, cooling and/or applying pressure to the tissue.

As used herein, "sheath" refers to a material capable of being applied to a region of tissue to be spectroscopically probed. A sheath can circumscribe a region of tissue, such as a fingertip or ear lobe. Alternatively, the sheath can conform to a surface of tissue, and be held in place with straps, adhesive or other material.

As used herein, "flexible" refers to the property of a sheathing material allowing it to adopt various conformations.

As used herein, "secured" to a region of tissue means that the device will be capable of maintaining steady and continuous contact with the tissue for a period of minutes such that reasonably reliable measurements can be taken from the tissue. The device may be applied to the tissue, as a fingerstall fitted to a fingertip. Alternatively, the tissue may be applied to the device, as a fingertip placed in a molded sample holder or strapped to a solid surface.

As used herein, "heat transfer fluid" is a thermally stable, electrically insulating fluid that facilitates distribution of heat or cold.

As used herein, "window" means an opening (absence of material) or a transparent material. The material is sufficiently transparent if electromagnetic radiation can be passed from a first side of the window, through the material to tissue of a subject positioned on the second side of the window, and light scattered by the tissue can be detected at or near the first side of the window.

As used herein, "phase transition" or "order-disorder transition" refers to relative orientation and rigidity of arrangement of lipid side chains in interstitial fluids; capillary walls, membranes, blood, liposomes, etc.

As used herein, "a" means at least one, and can include a plurality.

Tissue Modulation Device

The invention disclosed herein provides a device that can be used for modulating temperature in a tissue. The device is suitable for use in conjunction with methods for measuring an analyte in the tissue. The device can be used noninvasively. The device is suitable for use during spectroscopy of tissue of a subject. In one embodiment, the device comprises an inner sheath, an outer sheath and a window disposed through the inner and outer sheaths, wherein the inner and outer sheaths comprise a sufficiently flexible material that the device can be secured to a region of tissue to be spectroscopically probed, wherein the inner and outer sheaths are joined to one another so that at least one temperature regulating element can be disposed between the inner and outer sheaths, and wherein the window is sufficiently transparent that electromagnetic radiation can be delivered to and collected from an underlying tissue through the inner and outer sheaths.

In a preferred embodiment, the device further comprises a temperature regulating element disposed between the inner and outer sheaths. The device can further comprise a temperature sensing element disposed between the inner and outer sheaths. Preferably, the temperature regulating element comprises wire, such as, for example, teflon-coated nichrome. The temperature regulating element can include a heating element, or a cooling element, or both a heating and cooling element provided in parallel. When both a heating element and a cooling element are employed, they can be under separate or coordinated control.

Preferably, the device further comprises a heat transfer fluid within the space between the inner and outer sheaths. Examples of heat transfer fluid include, but are not limited to, glycerol, silicone and oil, such as olive oil. The heat transfer fluid can comprise a deuterated molecule. Use of a deuterated molecule can avoid interference caused by Raman scattering due to the heat transfer fluid because the Raman spectra emitted by the deuterated molecule will be other than that of the light and the tissue. Preferably, the sheaths are sealed at the outer edges and around the window so that fluid cannot escape from between the inner and outer sheaths.

In one embodiment of the device, the window comprises a substantially annular opening or hole in the inner and outer sheaths. In another embodiment, the window comprises a lens. The window is preferably about 1 mm to about 10 mm in diameter. The lens can also be shaped so as to apply pressure to the tissue being probed, as a means of pressure modulation.

The inner and outer sheaths of the device can be substantially cylindrical in shape, comprise a fingerstall, and/or comprise a cuff. Preferably, the flexible material of the sheaths comprises latex. In preferred embodiments, the device is of similar dimensions to a finger cot, also known as a fingerstall. The flexible sheathing material allows for adaptation to various finger dimensions. Preferably, the overall length of the device is about 6 cm and the overall diameter at the open end is about 2 cm. The device can employ a plurality of sheathing materials.

In one embodiment, the inner and outer sheaths are separated by a gap of about 50 to about 1000 $\mu$m. An electrical connection to a thermocouple can be located near the open end of the apparatus. The gap between the two sheaths is preferably filled with approximately 1–2 ml of heat transfer fluid and the gap between the sheaths is sealed at the open end of the device where the finger is inserted as illustrated in FIGS. 1 and 2.

In another embodiment, the shape of the sheath is such that it fits snugly over the fingertip and up to the first finger joint. The inner and outer sheaths are connected around the wide end so that liquid does not leak out. In addition to the heating element, a thermoelectric cooler (such as a Peltier device) can be placed inside the two sheaths and separate electrical connections through the outer sheath can be made to the cooling element(s). Allowance is made for the electromagnetic radiation to contact the tissue through the window. Those skilled in the art can appreciate variations in the window that will permit bringing electromagnetic radiation into contact with the tissue for the purposes of taking measurements of emitted spectra.

In another embodiment, the device comprises means for altering the temperature of a region of tissue in a subject; means for securing the device to the tissue; and a window, wherein the window is sufficiently transparent that electromagnetic radiation can be delivered to and collected from an underlying tissue through the device. The means for altering the temperature of the region of tissue can comprise a heating element and/or a cooling element. The means for altering temperature can comprise a temperature regulating element as described hereinabove as well as any material capable of elevating or lowering the temperature of the tissue. In one embodiment, the means for securing the device to tissue comprises a sheath, a fingerstall, a cuff, a strap, a molded sample holder or an adhesive. Various modifications of the device can be made to accommodate different embodiments of the method. For example, the device can be used with a pressure-inducing device resembling a small blood pressure cuff or fitted to an inflexible device, such as a fixed position sample holder. Pressure and/or thermal modulation can be used to effect tissue modulation.

Figure 3:
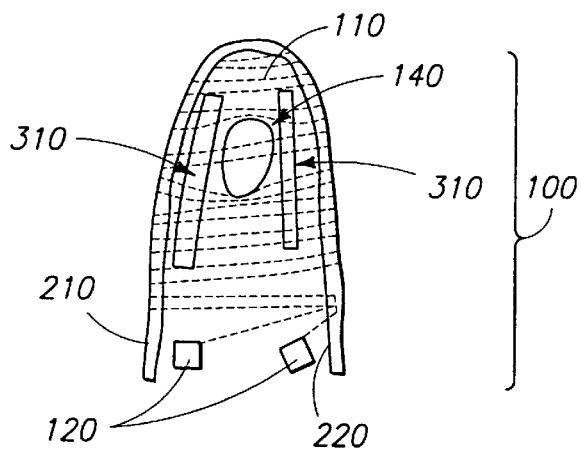
FIG. 3 is a bottom view of the tissue modulation device shown in FIG. 1.

A preferred embodiment of the device, which is designed to fit over a fingertip, is depicted in FIGS. 1–3. With reference to FIG. 1, a front view of the fingertip region shows the device 100, within which a heating wire 110 is coiled adjacent to the window 140 through which spectroscopic measurements can be taken. A first pair of electrical connections 120 are attached to the heating wire 110, and a second pair of electrical connections 130 are attached to a thermocouple.

FIG. 2 shows a side view of the same device 100 of FIG. 1. This view shows the heating wire 110 positioned to accommodate the window 140. Also shown are the electrical connection 120 and the outer sheath 210 and inner sheath 220. FIG. 3 shows a bottom view of the same device 100, in which the positioning of the cooling elements 310 can be seen along the sides of the window 140 and, in this embodiment, perpendicular to the coils of the heating wire 110. Also shown are the electrical connection 120 and the outer sheath 210 and inner sheath 220.

With respect to the particular embodiment for use with a fingertip that is illustrated in FIG. 3, the device can comprise a hole with sealed edges through which an optical device for electromagnetic radiation detection can be employed. Cooling elements are located on either side of the distal hole. Preferably, the cooling elements are about 3 to about 5 mm in length and are placed approximately 1–2 mm to either side of the hole. The cooling elements can be positioned all up and down the length of the finger as well.

In a preferred embodiment, the device is part of an apparatus or system that additionally includes means for irradiating the tissue with a light source and/or means for collecting and detecting light emitted by the irradiated tissue. One or more beamsplitters and additional lenses, filters and collimators can be introduced into the light path to modify the light entering and/or exiting the tissue.

Figure 5:
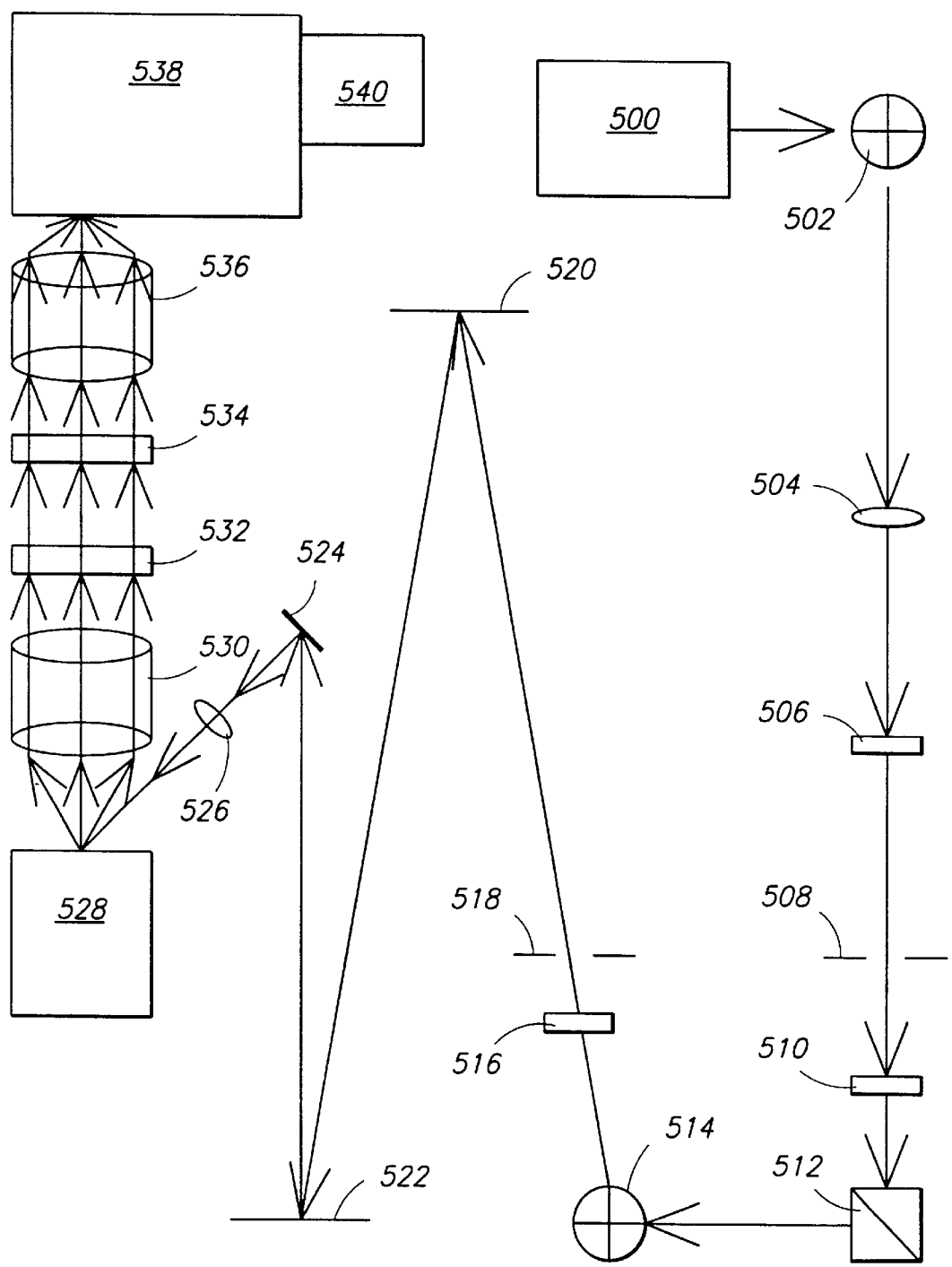
FIG. 5 is a schematic representation of a two-lens system for delivering light to and collecting light from a tissue for spectroscopic probing.

A schematic representation of a preferred system for spectroscopic probing of a tissue is depicted in FIG. 5. A source of electromagnetic radiation, such as a laser 500, directs light through a periscope 502. The periscope assists in alignment of the light with the entrance slit of the spectrograph 538. From the periscope 502, light then passes through a lens 504 having a long focal length, e.g., f=4.0 m, which corrects for divergence. The light then passes through a half-wave plate 506, which serves to rotate the polarization of the light to optimize function of the holographic bandpass filter. Next, light passes through an iris 508 and a metal/dielectric filter 510, both of which serve to remove light of undesirable wavelengths. Light then passes through a holographic bandpass filter 512, and a second periscope 514, which maintains alignment of the light with the entrance slit of the spectrograph 538. The polarization of the light is rotated again to achieve S-polarized light with respect to the entrance slit of the spectrograph 538 via a second half-wave plate 516. Light passes through another iris 518, a series of three mirrors 520, 522, 524 and a focussing lens 526, which focuses the light onto tissue in the sample holder 528, where the tissue modulation device would be positioned.

Emitted light is then made parallel by a camera lens 530 before entering a polarizer 532, the latter removing polarization shifted light. Light then passes through a holographic notch filter 534 to remove light that is not shifted in wavelength, and then through another camera lens 536, focussing light onto the spectrograph 538, to which a detector 540 is coupled. The detector can be, for example, a multi-channel or single channel detector. Examples of detectors include, but are not limited to, a CCD array, microbolometer array, an avalanche photodiode or a photomultiplier.

Methods of the Invention

The invention provides a method of measurement of blood volume simultaneously with measurements of a signal or signals indicative of blood analyte levels, conformation and states of aggregation. The blood volume measurement affords the necessary normalization of the blood analyte measurements to allow computation of concentration levels. The conformation and states of aggregation data can be related mathematically to lipid content and type and to protein content and type. Magnitude of measured changes as a function of temperature are approximately proportional to content.

Naturally occurring lipids, i.e. in a generic sense molecules with hydrocarbon chains (—CH2)—, have macroscopic chemical and physical properties determined by interactions between the chains on different molecules with each other as well as between the chains on lipid molecules and water. Similarly, proteins, as they occur in living tissues, are polymer molecules containing long chains of amino acids that have the tendency to assume particular structures due to hydrogen bonding interactions between successive amino acids with each other along the polymer and with water molecules in the surrounding solvent. Closely related forces (hydrophobic and hydrophilic) control these large scale structure determining interactions. The present invention uses a similar approach to probe noninvasively for the presence of these materials in living tissues.

Raman spectroscopy probes the vibrations of the atoms with respect to each other in molecules. As such, any forces that affect the energetics of the relative motions of atoms within molecules can potentially be manifest in the Raman spectra of those molecules. Such is the case with lipids and proteins. First, all lipids are known to possess at least some vibrational frequencies near 1400–1500 $cm^{-1}$, which correspond to the deformation of the atoms in the hydrocarbon chains from the standard arrangement of hydrogen tetrahedrally around each carbon atom. In the case of unsaturated fats (i.e. lipids) the preferred arrangement is not tetrahedral, but the exact preferred shape is not important to understand the proposed approach. In the case of proteins, by rotation around each of the bonds linking successive amino adds, i.e. "peptide linkages", various kinds of helical structures are produced. One of the vibrational modes that is most useful for determining the presence of the so-called "V-helix" in protein samples is well known to occur near ~1650 $cm^{-1}$.

The more varied the local chemical environment of the molecules, the more there are slight variations in the exact frequencies of these and other vibrational modes. As used herein, the term "local chemical environment" refers to interactions between adjacent molecules with each other, or to interactions between lipid and protein molecules with the water that is present in all in vivo settings. Whether involving protein or lipid, these interactions are fundamental electrostatic in nature and are well known as being either hydrophobic or hydrophilic.

In an in vivo solid, the most stable arrangements of adjacent lipid molecules predominate, resulting in fewer variations in the exact vibrational frequencies that are observed, compared to when the same molecules are in a more liquid or fluid environment. Similarly, at higher temperature, individual protein molecules assume less of the α-helix structure than at lower temperature, resulting mote variations in the exact vibrational frequencies that are observed compared to when the same molecules are at lower temperature. Thus, in either case, Raman features are generally sharper at low temperature than at higher temperature.

"Sharper" means here that Raman features revealing the frequencies of the vibrational modes in question span a narrower region of wavenumber ($cm^{-1}$) shift at low temperature than at high temperature. Since the number of modes does not change significantly, the strength of the Raman features becomes more intense at preferred frequencies, and less intense at frequencies corresponding to less stable arrangements with decreasing temperature. Whether referring to lipids or proteins, the absolute increase in strength is proportional to the number of molecules being probed. The present invention takes advantage of this relationship between increasing strength and number of molecules. By comparing Raman spectra obtained at physiological temperature to those obtained at a reduced, but, viable temperature, the data presented herein show that this effect can be observed noninvasively in in vivo human tissues.

These same modes can be observed with or without the temperature variation or modulation. The modes are always a direct measure of lipid or protein content in the probed region. However, this measure is undifferentiated with regard to tissue depth and, in some case, thereby in tissue type, i.e. blood versus skin. Differentiation can be obtained based on optical tactics like confocal imaging, temperature modulation, or using the two in combination. The temperature modulation allows differentiation based on the relative cooling behavior of the more external tissues compared to the deeper, better thermally controlled tissues, i.e. blood. Since one can always observe the Raman spectrum due to the total lipid content, by subtraction of the amount of Raman modulation induced by the temperature variation, one can differentiate between the easily cooled tissues and the less easily cooled tissues.

This approach can be combined with other non-temperature based techniques of tissue modulation to differentiate between blood and static tissues, so that in combination, a much more complete and differentiated quantitative picture of the composition and form of the tissues can be obtained noninvasively. By observation of the relative Raman variations for various tissue samples, this spectroscopic approach can be calibrated to an absolute scale using established invasive chemical and physical techniques.

Raman spectroscopy can be used to obtain information about fatty acids and phospholipids (see Tu, A.T., 1982, Raman Spectroscopy in Biology, John Wiley & Sons, NY). The 2850 $cm^{-1}$ Raman band is the C—H symmetrical stretching mode, and is relatively constant in intensity under varying temperatures. The intensity ratio of 2890 and 2850 $cm^{-1}$ bands is used to monitor the transition, temperature, that is melting temperature, of lipids and phospholipids (Brown, K. G. et al., 1973, Biochem. Biophys. Res. Commun. 54:358; Larsson, K., 1973, Chem. Phys. Lipids 10:165; Mendelsohn,. R., 1973, Nature 243:22). The ratio of 2890 $cm^{-1}$ band to 2850 $cm^{-1}$ band will shift as a function of temperature, decreasing as temperature rises. A plot of this ratio as a function of temperature will shift toward higher ratios at higher temperatures for saturated fats and plain lipids, while shifting in the opposite direction for unsaturated fats and phospholipids. Thus, the noninvasive methods of the invention can be used to obtain information about the identity and content of lipids in a subject.

Likewise, temperature shifts can be used to detect protein changes that occur when temperature is altered. For example, the alpha-helical structure of proteins is relaxed upon temperature elevation, as discussed in Shoemaker, D. P. et al., 1996, Experiments in Physical Chemistry, $6^{th}$ Ed., McGraw-Hil, New York, pp. 326–334, and references cited therein.

Temperature and pressure can be used to affect the capillary content and, although these can be controlled to a large extent, it till be desirable to devise specific apparatus to aid in normalization. The present invention allows a normalization that is less vulnerable to error due to differences between individual anatomy and blood flow patterns. It also aids in the integration of the mechanical requirements for tissue modulation with the optical system needed to affect the blood/fluid/tissue analyte measurements.

The method comprises irradiating the tissue in a blood-replete state (warm, or no pressure) with electromagnetic radiation having an excitation wavelength and collecting the spectra emitted by the tissue in the blood-replete state (warm, or no pressure). The method further comprises irradiating the tissue in a blood-depleted (cool, or pressured) state with electromagnetic radiation having an excitation wavelength and collecting the spectra emitted by the tissue in the blood-depleted (cool, or pressured) state. The method additionally comprises analyzing the collected spectra to determine a concentration of analyte present in the tissue, wherein the analyzing comprises determining the difference between the spectra collected in the blood-replete (warm) and blood-depleted (cool) states. Examples of spectra that can be collected include, but are not limited to, Raman, nuclear magnetic resonance (NMR), electron spin resonance (ESR), UV-visible absorption, infrared absorption, fluorescence and phosphorescence spectra.

In preferred embodiments, the tissue is blood, such as blood circulating in capillary beds of the fingertip. Other tissues can be used, such as ear lobe, muscle, skin, breast or brain. The subject is preferably a vertebrate, such as a mammal, bird, reptile or fish. Examples of mammals include, but are not limited to, human, bovine, porcine, ovine, murine, equine, canine, and feline. In a most preferred embodiment, the subject is human.

Figure 4:
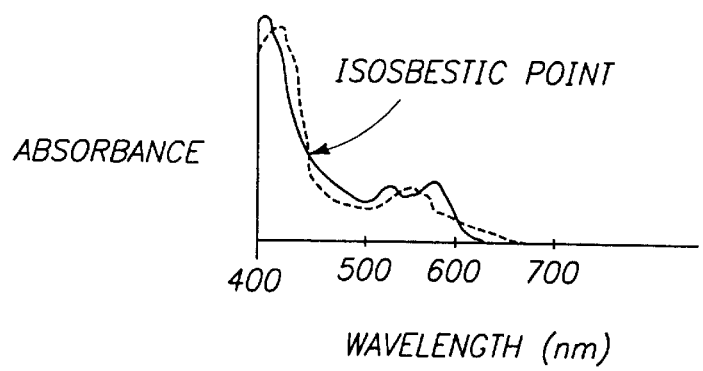
FIG. 4 is a graph illustrating the determination of an isosbestic point.

In preferred embodiments, the analyzing employs the determination of blood volume by contacting the tissue modulated region with light chosen to have a wavelength at an isosbestic point of, for example, the oxydeoxyhemoglobin binary equilibrium (805 and 580 nm), as demonstrated in FIG. 4. The amount of light which returns is approximately inversely related to the volume of blood in the contacted region.

In one embodiment, the invention provides a method of modulating temperature of tissue in a subject to be spectroscopically probed. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue. The collected Raman spectra can then be analyzed, the analysis including a comparison of spectra emitted in the different temperature states.

The invention also provides a method for monitoring phase transitions and conformational changes, and thereby a method for determining lipid content and identity and protein content and identity in a tissue of a subject. In a preferred embodiment, the method comprises applying a tissue modulation device of the invention to the tissue, passing current through the temperature regulating element so as to elevate or lower the temperature of the tissue, and passing electromagnetic radiation through the window of the device. Preferably, spectroscopic probing is performed when the temperature of the tissue has been elevated or lowered and when the temperature of the tissue is not elevated or lowered. The method can further comprise collecting Raman spectra emitted by the tissue.

The collected spectra are then analyzed to determine the lipid content, lipid identity and/or protein identity, protein content of the tissue. Preferably, the analysis comprises determining the difference in number of Raman shifted photons emitted by the tissue at different temperatures. For information related to non-mobile tissues, the data of greatest interest is that collected during the period of temperature modulation (e.g., hatched area under curves shown in FIGS. 14 and 15). For information related to mobile tissues, such as blood, the analysis preferably includes subtraction of the data relating to non-mobile tissues from the total spectra collected (e.g., entire curve shown in FIGS. 14 and 15). The integral of the area under such curves provides an indication of the relative content of lipid or. protein, and these values can be compared to measurements obtained using standard invasive procedures for calibration. Once a calibration has been established from a sample of subjects, content information can be obtained at future times from the same or different subjects without requiring any invasive procedures.

Information about the depth of the source of spectra collected from the tissue can be obtained as well, through the use of a confocal system. One example of such a confocal system is that described in Example 2 and FIG. 12. This depth information facilitates identification of the type of tissue (e.g., skin, blood) and type of lipid or protein responsible for the measured values.

EXAMPLES

The following examples are presented to illustrate the present invention and to assist one of ordinary skill in making and using the same. The examples are not intended in any way to otherwise limit the scope of the invention.

Example 1

Raman Shift Observed With Temperature Modulation

This example illustrates the order-disorder transition of lipids at least 6–30 microns beneath the surface of the skin using purely thermal modulation. The results show that noninvasive in vivo Raman spectroscopy can be used to obtain information about the identity and content of lipids.

Mat & Methods

A schematic diagram of the optical set up is shown in FIG. 5. A 785 nm, amplitude and wavelength stabilized, external cavity, CW laser 500, (SDL XC-30; SDL Inc., San Jose, Calif.) produces a maximum total power of 300 mW. More than half of this power is associated with a large, spectrally wide and unsymmetrical base of amplified spontaneous emissions (ASE). This is adequate to obtain Raman spectra of simple, less challenging samples, i.e. virtually any in vitro sample. To obtain acceptable in vivo spectra, however, a substantial amount of the ASE should be removed. This is done using a holographic bandpass filter 512 (Kaiser Optical Systems, Ann Arbor, Mich.). While this does not remove all of the disturbing background radiation, it is adequate to allow in vivo spectra to be obtained.

Optics for correcting the spatial arrangement of the fast and slow axes of the laser divergence, as well as for obtaining the optimum polarization for diffraction efficiency and background reduction in the f1.4 holographic spectrograph 538 (Holospec, Kaiser Optical Systems, Ann Arbor, Mich.), eventually allow us to bring only about 50 mW of laser power to the sample. All optics are antireflection coated for 785 nm and a 13 cm focal length lens 526 is used to finally bring the light to the tissue in question. An angle of incidence of approximately 53' gives acceptable results. The light collection system uses two 50 mm f1.4 Nikon camera lenses 530, 536, a holographic notch filter 534 (Kaiser Optical Systems, Ann Arbor, Mich.) and a Polacor™ (Corning) polarizer 532 to bring the scattered light from the sample to the entrance of the spectrograph 538. The detection system 540 is an IR enhanced, liquid nitrogen cooled CCD array from Princeton Instruments. The resolution of the spectrograph system is 6 $cm^{-1}$ with wavenumber accuracy of 6 $cm^{-1}$ using a calibration based on known lines in atomic emission spectra.

The samples for all the experiments reported in this example were the fleshy side of the finger tips of human subjects, on the side opposite the finger nail. Essentially identical results were obtained using any of the fingers and either hand. The sample holder 528 itself, which we have termed the tissue modulator (TM), is important to obtaining reproducible results for either of the two types of experiments presented in this example. The TM combines the electromechanical elements required to perform tissue modulation with a set of focussing optics to bring the excitation light to the sample so that precise optical alignment can be maintained throughout the procedure.

The TM used for this example contains an orifice, against which the finger tip is placed, so that the tissue to be interrogated is accessible to the 785 nm excitation light through the orifice. There is a spring loaded plunger arrangement which can be placed in a retracted position so that it does not place pressure against the back of the finger. Alternatively, the plunger can be released so that a padded, complementary shaped piston presses against the back and side surfaces of the finger, thereby aiding the volunteer in squeezing the finger tip against the orifice. Any difference in absolute position of the finger surface in either plunger position was found to be negligible and irrelevant.

When the finger is simply placed in the TM without any pressure between the finger and the orifice, the finger is in the unsqueezed state. In this state, the blood volume is normal and the flow patterns and net rate into and out of the region is normal. When the plunger is released, and the volunteer presses the finger against the orifice, the blood flow to the 785 nm exposed finger tip is restricted, and at equilibrium, the blood and fluid content, and possibly the chemical nature, e.g. oxygenation, of those fluids in the region inside the orifice is changed. The finger is then in the squeezed state.

To achieve good mechanical pressure modulation, the total pressure involved varies somewhat from sample to sample but never exceeds about 1 Newton. The TM has a built-in stop that the user can adjust to obtain optimal pressure with an acceptable comfort level for the squeezed state. When the plunger is retracted, the subject places his or her finger just touching against the orifice and holds it motionless while the spectrum is obtained. Different sized and shaped orifices are optimal for different size fingers and different types of tissue modulation. For the present results, a round orifice 0.95 cm in diameter was used and the average finger was 5.3 cm in circumference.

Visual inspection shows that, regardless of the shapes, in the squeezed state there is always a pale blood depleted region, within a millimeter, just adjacent to where the orifice edge makes physical contact with the skin surface. A circularly shaped orifice, of appropriate size relative to the size of the finger tip, also produces in the squeezed state a circular area inside the blood depleted edge region which, still contains some blood. The amount of blood inside this region is not precisely known at this time but should be somewhat less because of the net applied pressure. For the present, it is clear that there is a gradient of blood volume between this inner region and the outer depleted region.

Visual inspection using an in-line video system with magnification shows that when the system is aligned initially in the unsqueezed state, the light impinges near the center of the orifice. In going to the squeezed state, i.e. the volunteer doing nothing more than pushing against the TM orifice, the point where the excitation laser contacts the finger tip moves slightly, impinging into the blood depleted region. The results show that moving and changing how the laser contacts the finger tip without increasing the pressure between the finger tip and the orifice results in no modulated spectrum. Therefore, in the squeezed state the laser interacts with a blood depleted region compared to the unsqueezed state.

Results

Among the test subjects used in this example are several Caucasian adults of varying heights and weights and an African American male and female. All of the subjects were in good health at the time of their participation and, with respect to the laser excitation, none experienced pain or discomfort of any kind during or after the testing. The results for the different individuals are all essentially identical. Experiments were performed utilizing mechanical pressure and temperature as tissue modulating stimuli.

Figure 6:
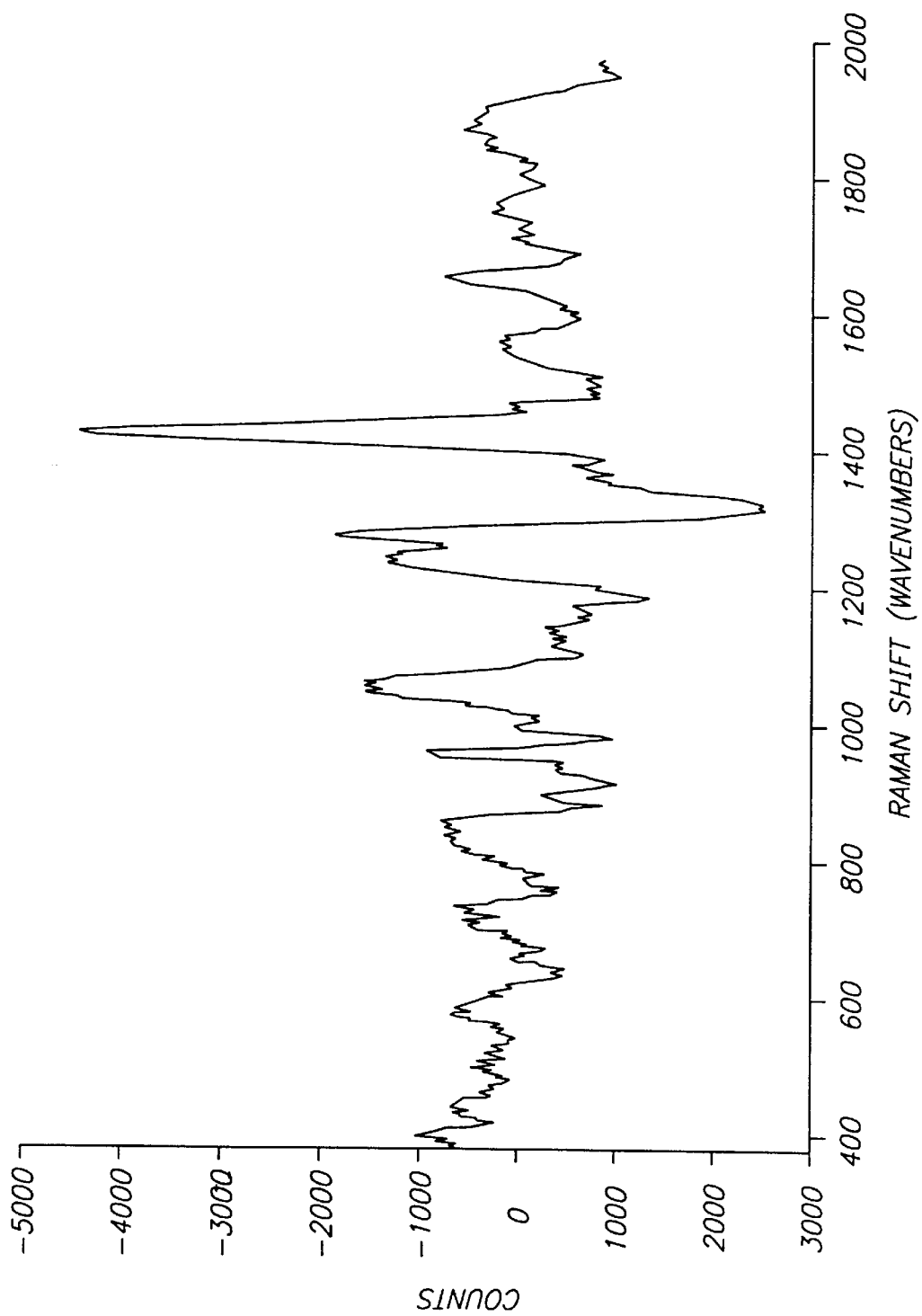
FIG. 6 is a graph showing the number of Raman shifted photons at wavenumbers below 2000 $cm^{-1}$ after subtracting measurements taken from a cooled finger tip from measurements taken from the same finger tip at room temperature.

Representative results obtained from a single subject exposed to temperature modulation (no finger pressure applied) are shown in FIGS. 6–11. Raman spectra were collected over a period of 6 minutes from the subject's finger tip at room temperature, and for an additional 6 minute period after cooling. The finger tip was cooled by placing it in a glass of ice water for a few minutes until the subject could no longer tolerate the cold. FIG. 6 shows the number of Raman shifted photons (counts) at various wavenumbers after subtraction of measurements taken in the cold condition from those taken at room temperature. The peaks observed at approximately 1050 and just above 1400 correspond to peaks known from in vitro studies to occur as a result of a temperature shift. The peaks observed just above 1200 provide information about lipids, which congeal at cooler temperatures, and also proteins, which are denatured at higher temperatures.

An empirical baseline subtraction procedure was used in the analysis. Each raw spectrum was subjected to a 101 point adjacent averaging smoothing algorithm. Each smoothed resultant was subtracted from the corresponding original raw spectrum and the difference subjected to a 7 point adjacent averaging smoothing algorithm. While the smoothed difference of the raw spectra was identical to the difference between the smoothed raw spectra, only the smoothed version of the difference was used in the analysis. Consideration of only the smoothed version of the difference between the raw spectra avoids introduction of differences between potential artifacts introduced by empirical baseline subtraction.

Other baseline subtraction procedures were employed, such as nonlinear least squares, to approximate the shape of the raw curves with a log normal or binomial distribution and other functions. Using these functions to perform the same subtraction procedure obtained results consistent with those shown in FIG. 6. Application of the pure smoothing based procedure to a spectrum consisting of one narrow peak on a simulated background reveals a well-known tendency to introduce small negative dips on either side of the real peak. The depth of these artifacts depends on the relative size of the broad background and the narrow feature. Given this predictable behavior as a caveat, the spectra disclosed herein can be compared with others in the literature. Another strategy is to perform the method using longer wavelength excitation, thereby inducing less broadband fluorescence.

Figure 7:
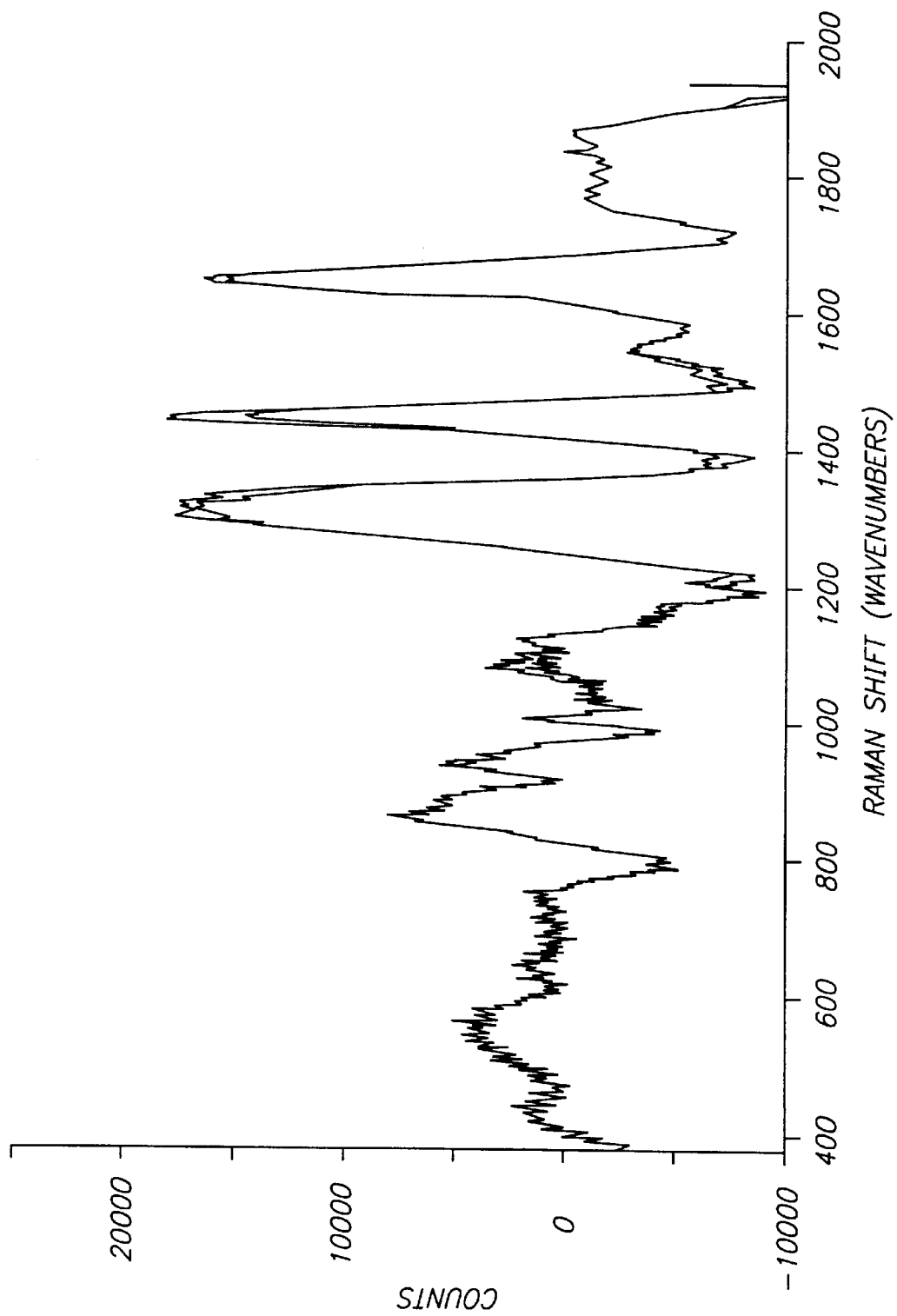
FIG. 7 is a graph showing the data of FIG. 6 in raw form (prior to subtraction). The upper trace (see peak near 1450 $cm^{-1}$) shows spectra collected from cooled tissue. The lower trace shows spectra collected at room temperature.
Figure 8:
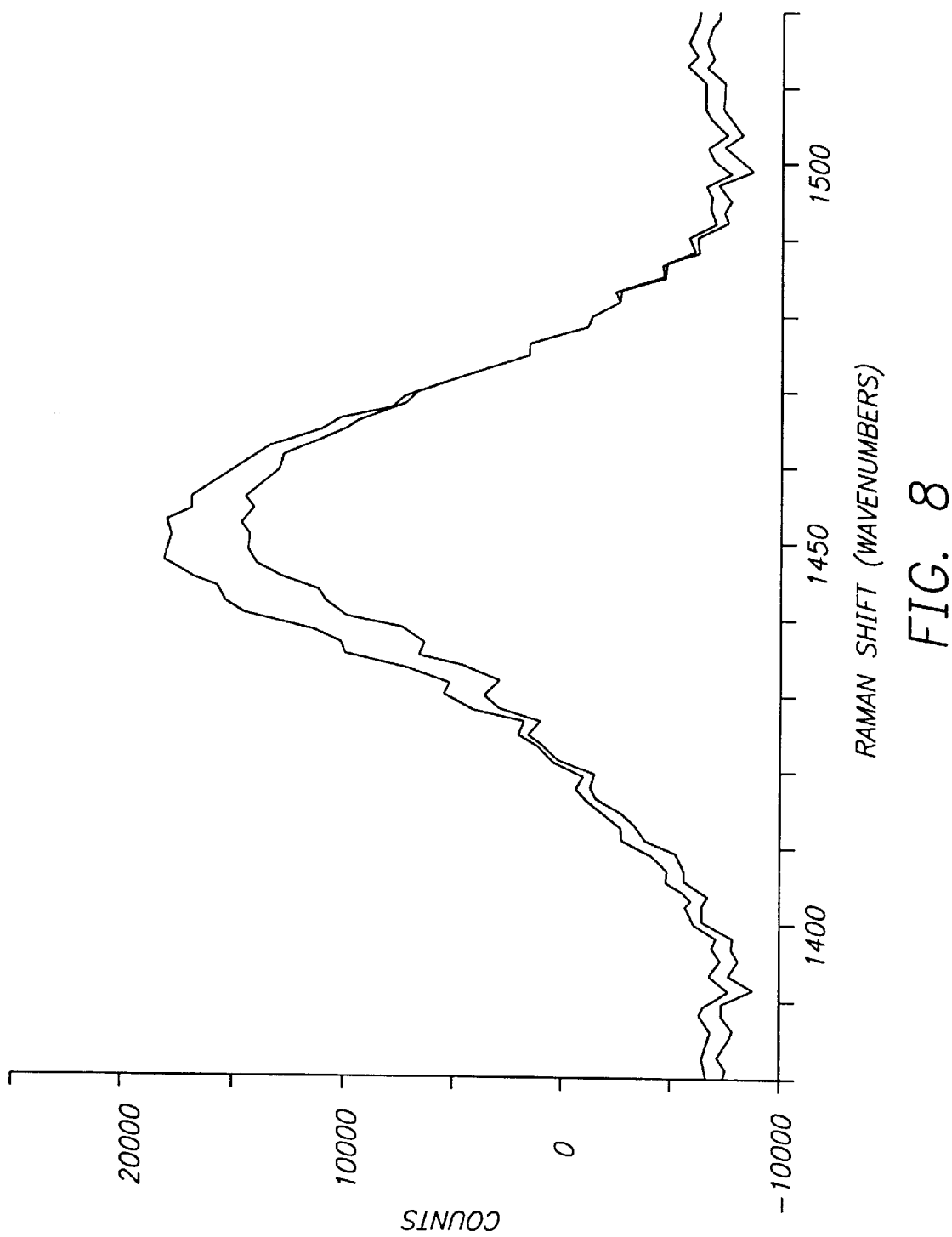
FIG. 8 is a graph showing the data of FIG. 7, but expanded to show the region of spectra near 1450 $cm^{-1}$.
Figure 9:
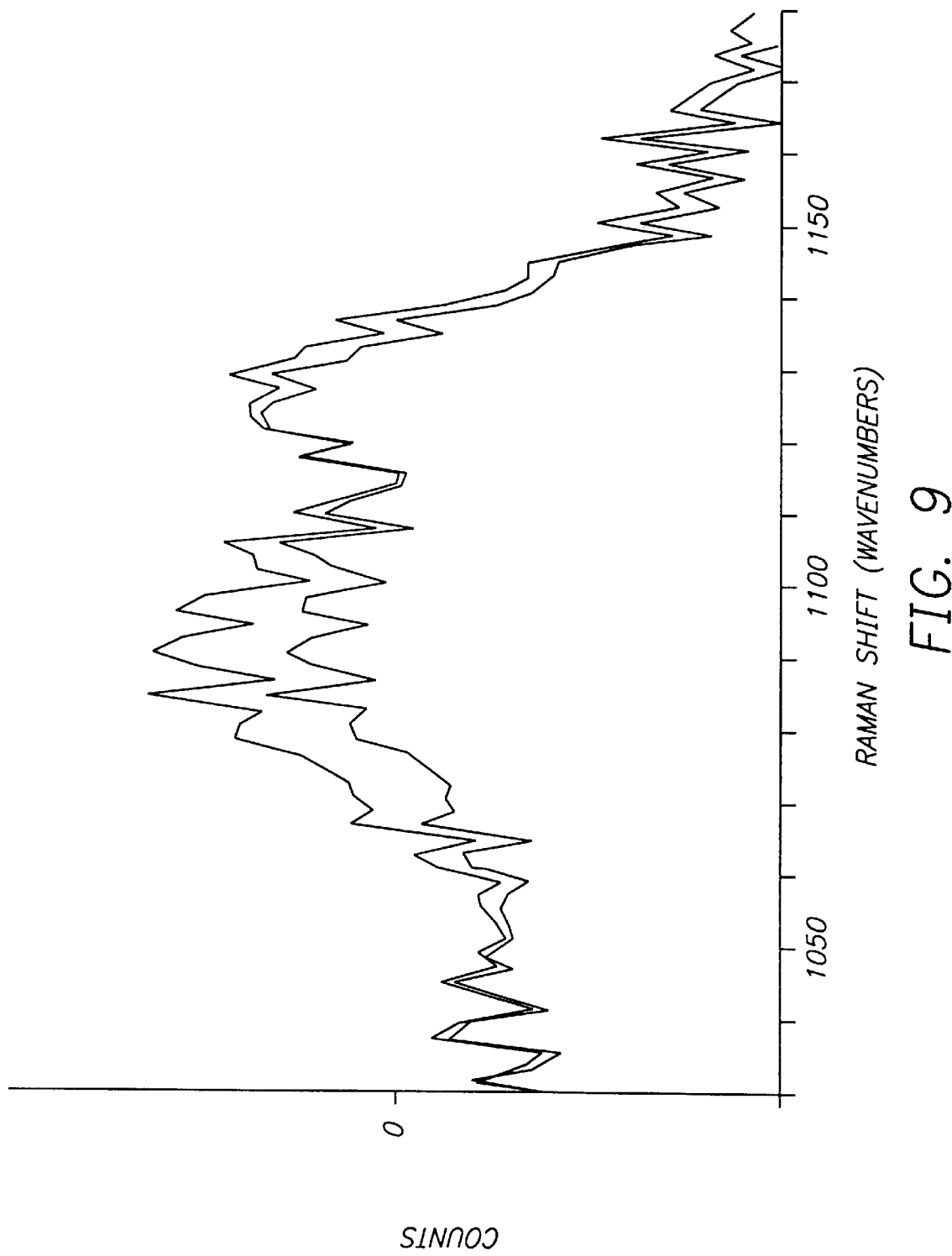
FIG. 9 is a graph showing the data of FIG. 7, but expanded to show the region of spectra near 1100 $cm^{-1}$.
Figure 10:
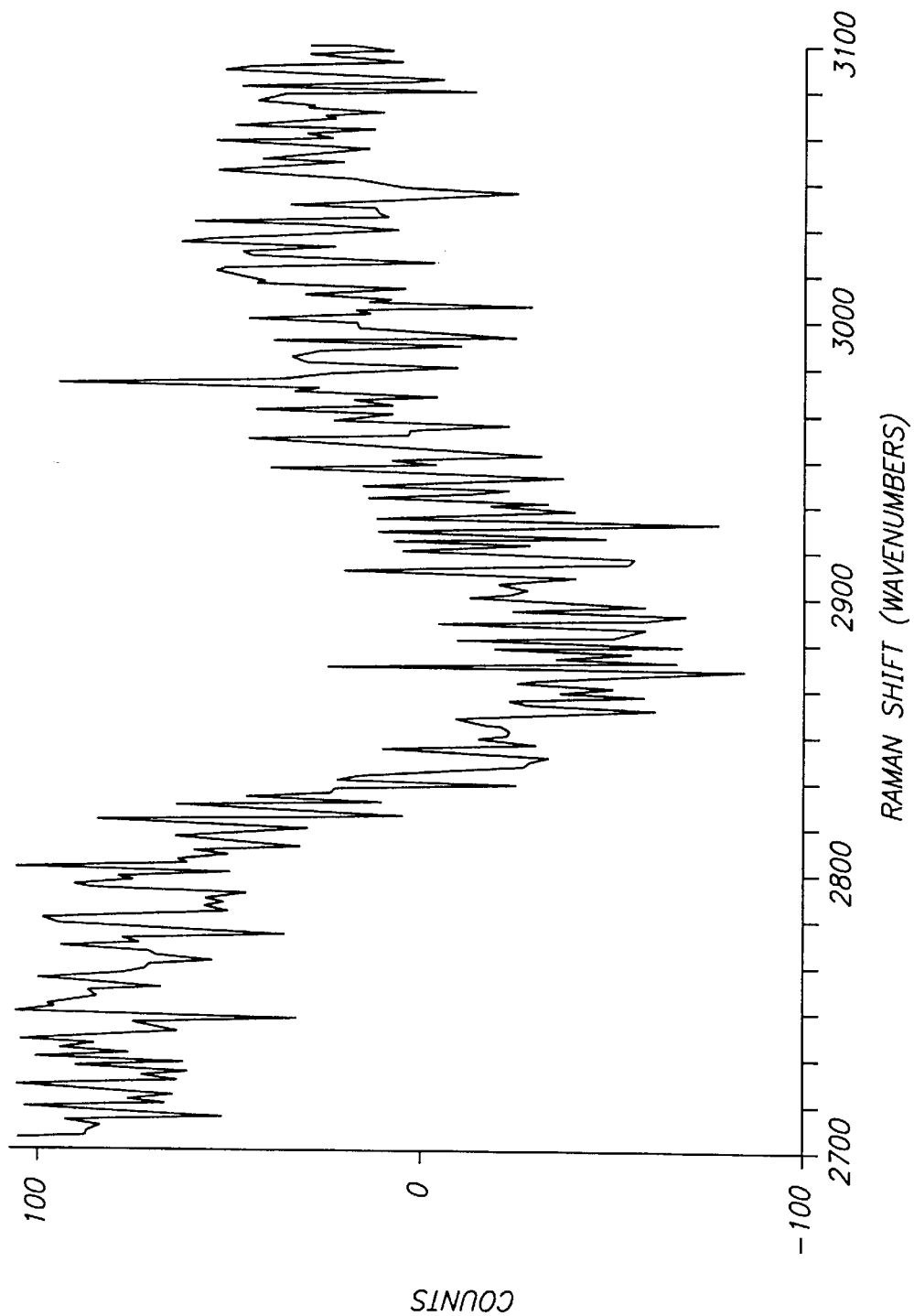
FIG. 10 is a graph showing the long shift data corresponding to the data shown in FIG. 6.
Figure 11:
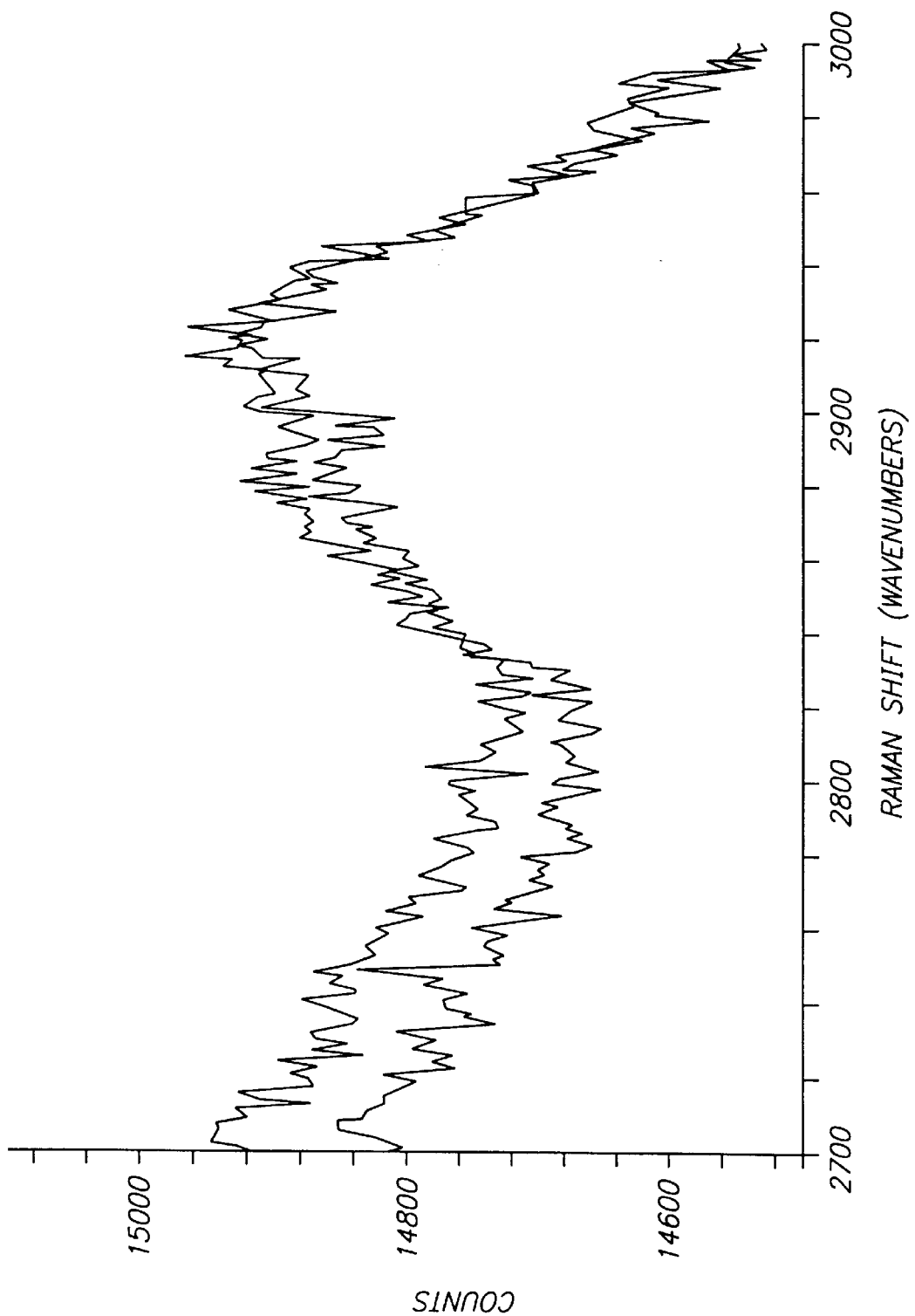
FIG. 11 is a graph showing the data of FIG. 10 in raw form (prior to subtraction). The trace that is lower at 2700–2800 $cm^{-1}$ and higher near 2900 $cm^{-1}$ shows data collected when the tissue was cooled, and the other trace shows data collected at room temperature.

FIG. 7 shows the same data as shown in FIG. 6, except in raw form, depicting separate traces for counts obtained at 0–2000 wavenumbers in the cold condition (upper trace) and at room temperature (lower trace). In FIG. 8, the x-axis is expanded to show the difference between these two traces near 1450 wavenumbers. FIG. 9 shows the difference near 1100 wavenumbers. FIG. 10 shows data as depicted in FIG. 6, but at higher wavenumbers. Note the peak at approximately 2980. FIG. 11 shows the same data as in FIG. 10, except in raw form, depicting separate traces for counts obtained at higher wavenumbers. The trace that is the upper trace at wavenumbers near 2900 is from the cold condition. Note that these data were obtained in just 17 seconds, indicating the speed with which these noninvasive measurements can be completed.

Example 2

Depth Discrimination

This example describes a confocal, four-lens system that can be used to determine the depth of a signal emitted by tissue that is spectroscopically probed. Determination of the depth of a source of emitted light permits identification of the type of tissue, e.g., skin, blood, and of the type of lipid, e.g., lipid, phospholipid, sphingolipid.

Figure 12:
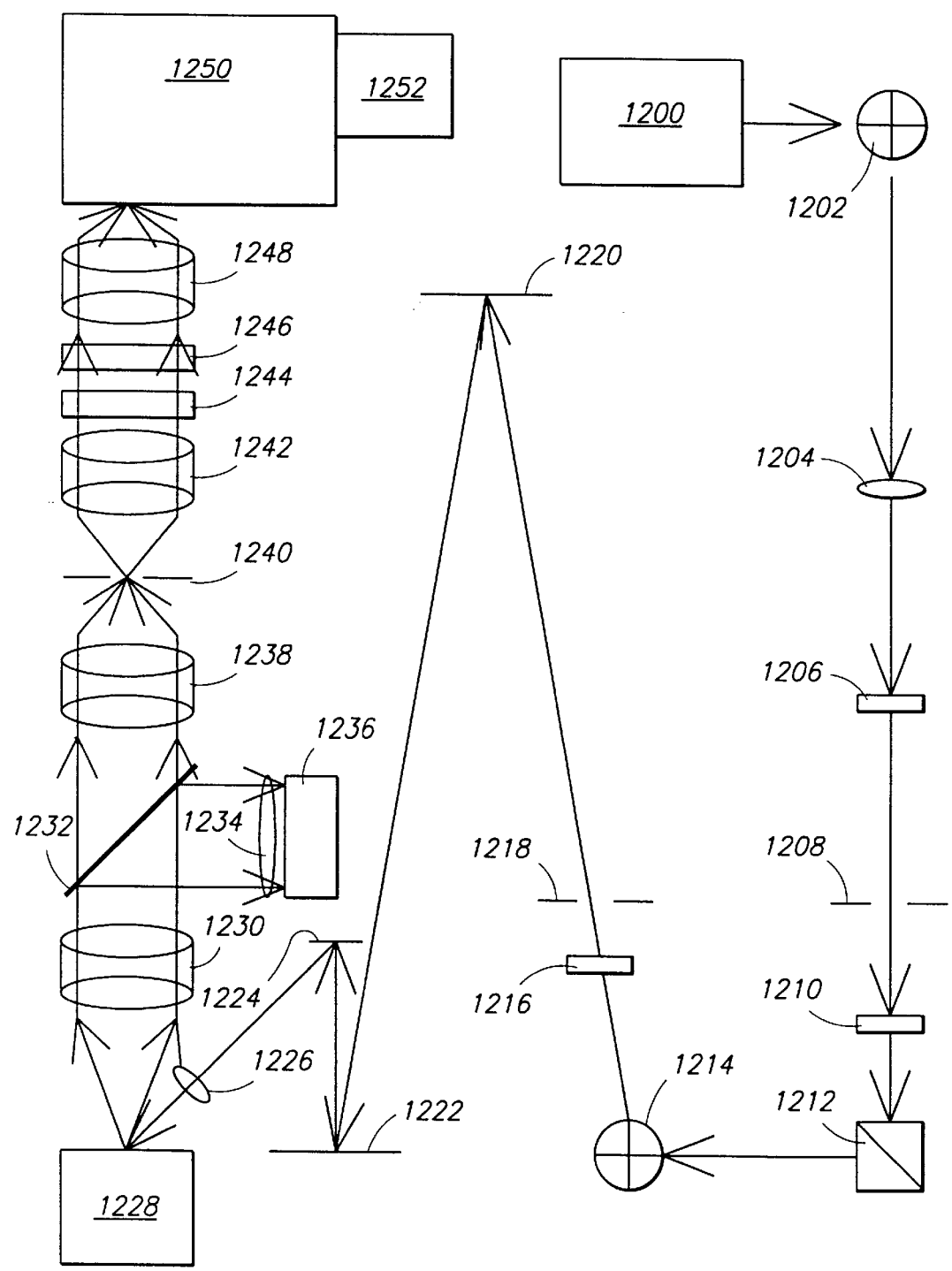
FIG. 12 is a schematic representation of a confocal, four-lens system for combining depth discrimination with spectroscopy.

A schematic representation of such a confocal, four-lens system is shown in FIG. 12. Light is directed from a laser source (SDL-XC30) 1200 to a periscope 1202, then through a 4 meter lens 1204, a half-wave plate 1206, in iris 1208, a metal/dielectric filter 1210, a holographic bandpass filter 1212, a second periscope 1214, a second half-wave plate 1216, a second iris 1218, a series of three mirrors 1220, 1222, 1224, and a focussing lens 1226, before arriving at the tissue, which is positioned in the sample holder 1228 (tissue modulation device). Light emitted by the tissue passes through a camera lens 1230 and on to a pellicle 1232, which directs some of the light to a CCD imaging camera 1236 after passing through a lens 1234. The remaining light from the tissue is directed through a second camera lens 1238, a confocal iris 1240, a third camera lens 1242, a polarizer 1244, a holographic notch filter 1246, and a fourth camera lens 1248, before the light enters the holographic spectrograph 1250 having a light collection efficiency of f=1.4, to which is coupled a CCD detector 1252.

Example 3

Non-invasive Protein and Lipid Determination

This example demonstrates the use of spectral emissions from a fingertip to obtain information that is proportional to blood volume, protein content and lipid content. Data were collected from a human subject's fingertip before, during and after cooling by immersion in an ice bath.

Figure 13:
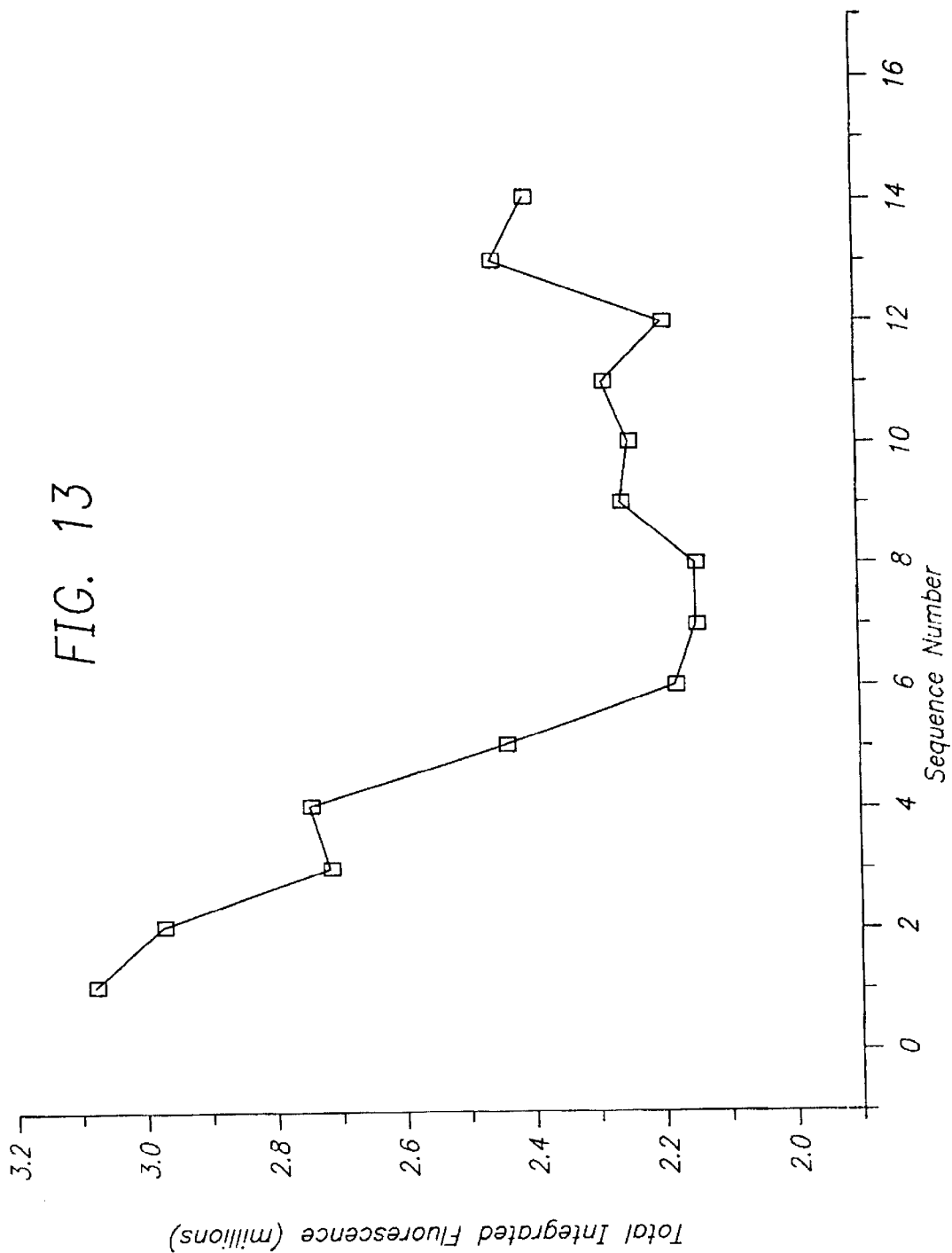
FIG. 13 is a graph showing total integrated fluorescence, in millions, measured at each interval, indicated as sequence number, from the fingertip of a human subject. The first two measurements were taken before cooling, the next four while cooling, and the remainder after withdrawal from the ice bath and allowing the fingertip to warm in a room temperature environment.

FIG. 13 shows total integrated fluorescence, in millions, measured at each interval, indicated as sequence number. Spectra for each measurement were collected for a period of 30 seconds. During the cooling portion of the procedure, these 30 seconds periods of spectra collection were preceded by a 30 second period of cooling. The first two measurements were taken before cooling, the next four while cooling, and the remainder after withdrawal from the ice bath and allowing the fingertip to warm in a room temperature environment. These total fluorescence measurements indicated changes in blood volume of the fingertip as temperature of the tissue changes. The blip observed at sequence number 4 reflects cold-induced vasodilation, confirming that the measurements reflect blood volume changes. The data shown in FIGS. 14 and 15 were taken from the same fingertip, under the same conditions.

Figure 14:
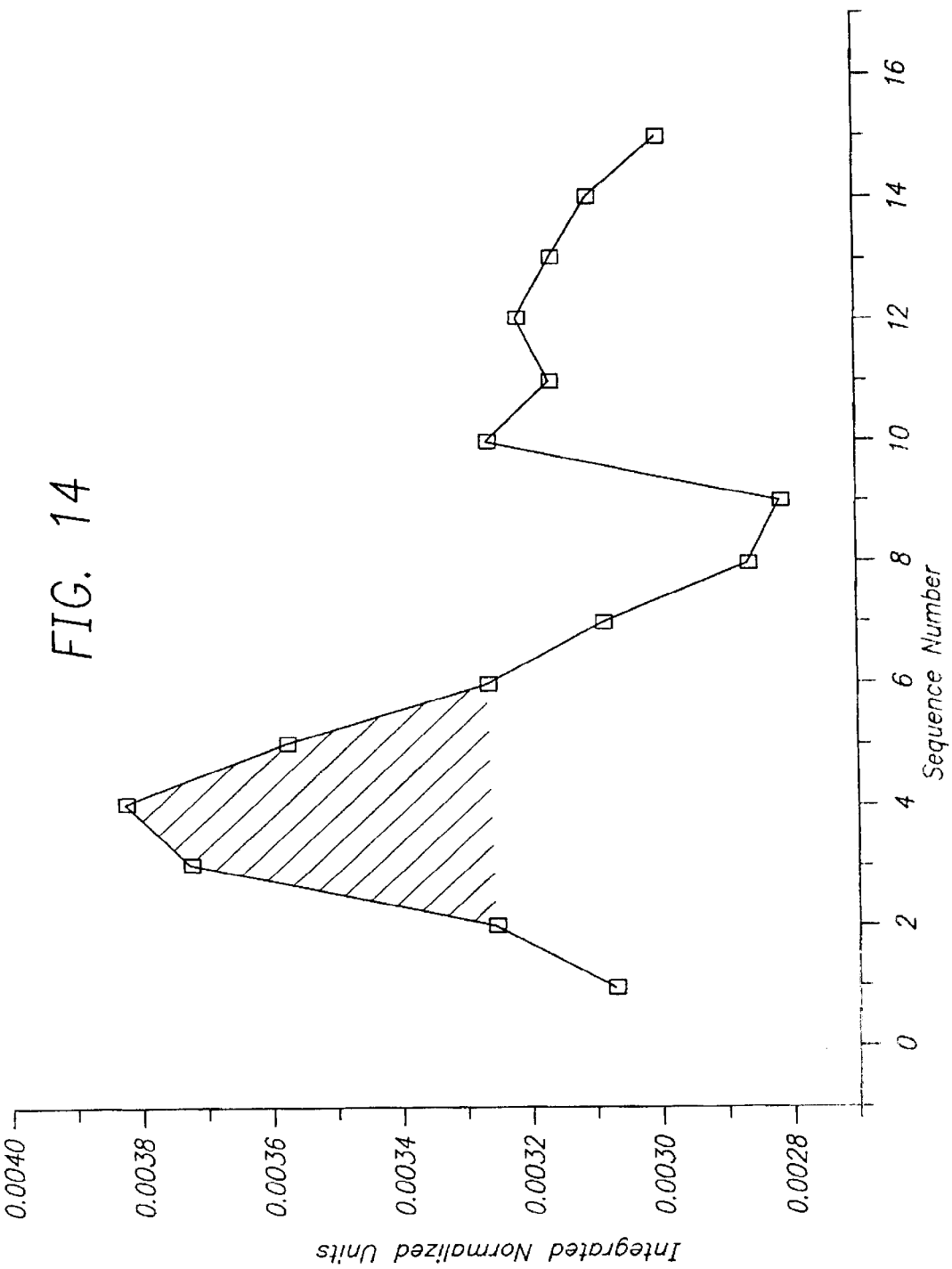
FIG. 14 is a graph showing Raman spectra collected at 1610–1700 $cm^{-1}$, in integrated normalized units, over the same sequence of measurements as shown in FIG. 13.

FIG. 14 shows Raman spectra collected at 1610–1700 cm$^{-1}$, in integrated normalized units, over the same sequence of measurements. The hatched area indicates the intervals during which temperature was dropping and information corresponding to protein content was obtained. The integral of this area corresponds to protein content, as is known from in vitro data (Shoemaker, D. P. et al., Experiments in Physical Chemistry, 6$^{th}$ Ed., McGraw-Hill, NY, 1996, pp. 326–334, and references cited therein). The normalized units were calculated by dividing the obtained values by the total fluorescence of that sample.

Figure 15:
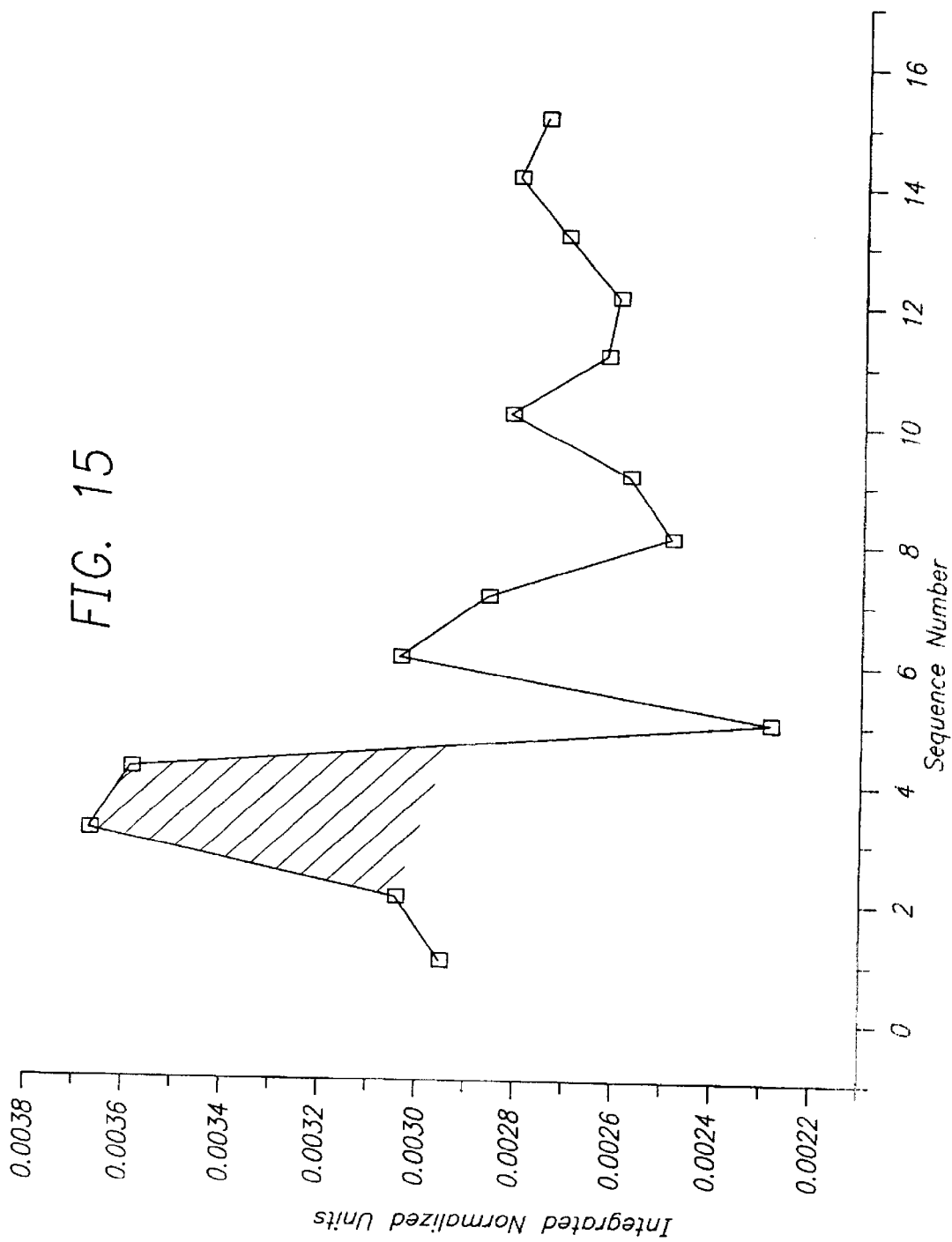
FIG. 15 is a graph showing Raman spectra collected at 1450–1500 $cm^{-1}$, in integrated normalized units, over the same sequence of measurements as shown in FIG. 13.

FIG. 15 shows Raman spectra collected at 1450–1500 cm$^{-1}$, in integrated normalized units, over the same sequence of measurements. The hatched area indicates the intervals during which temperature was dropping and information corresponding to lipid content was obtained. The integral of this area corresponds to lipid content, as discussed above.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of determining relative lipid content of tissue in a subject comprising:
   (a) contacting the tissue with electromagnetic radiation having an excitation wavelength;
   (b) collecting the Raman spectra emitted by the tissue in a range of wavelengths associated with lipids;
   (c) altering the temperature of the tissue;
   (d) repeating steps (a) and (b) while the temperature of the tissue is altered; and
   (e) analyzing the spectra collected in steps (b) and (d) to determine a relative amount of lipid present in the tissue.

2. The method of claim 1, wherein the analyzing comprises determining the difference in number of Raman shifted photons emitted by the tissue in steps (b) and (d).

3. The method of claim 1, wherein the range of wavelengths associated with lipids is about 1450–1500 cm$^{-1}$ or about 2890–2850 cm$^{-1}$.

4. The method of claim 1, wherein the temperature of the tissue is altered by cooling.

5. The method of claim 4, wherein the tissue is cooled to about 2 to about 12° C.

6. The method of claim 1, further comprising determining the depth of a source of the spectra emitted by the tissue.

7. The method of claim 6, wherein the determining comprises using a confocal lens system to collect emitted spectra.

8. The method of claim 6, wherein the analyzing further comprises determining the type of lipid present in the tissue based on the depth of the source of the spectra emitted by the tissue.

9. The method of claim 1, wherein the tissue is a fingertip.

10. A method of determining relative protein content of tissue in a subject comprising:
    (a) contacting the tissue with electromagnetic radiation having an excitation wavelength;
    (b) collecting the Raman spectra emitted by the tissue in a range of wavelengths associated with protein;
    (c) altering the temperature of the tissue;
    (d) repeating steps (a) and (b) while the temperature of the tissue is altered; and
    (e) analyzing the spectra collected in steps (b) and (d) to determine a relative amount of protein present in the tissue.

11. The method of claim 10, wherein the analyzing comprises determining the difference in number of Raman shifted photons emitted by the tissue in steps (b) and (d).

12. The method of claim 10, wherein the range of wavelengths associated with protein is about 1610–1700 cm$^{-1}$.

13. The method of claim 10, wherein the temperature of the tissue is altered by cooling.

14. The method of claim 13, wherein the tissue is cooled to about 2 to about 12° C.

15. The method of claim 1, further comprising determining the depth of a source of the spectra emitted by the tissue.

16. The method of claim 15, wherein the determining comprises using a confocal lens system to collect emitted spectra.

17. The method of claim 15, wherein the analyzing further comprises determining the type of protein present in the tissue based on the depth of the source of the spectra emitted by the tissue.

18. The method of claim 10, wherein the tissue is a fingertip.

* * * * *

UNITED STATES PATENT AND TRADEMARK OFFICE
CERTIFICATE OF CORRECTION

PATENT NO.      : 6,389,306 B1                                       Page 1 of 1
DATED           : May 14, 2002
INVENTOR(S)     : Joseph Chaiken and Charles M. Peterson It is certified that error appears in the above-identified patent and that said Letters Patent is hereby corrected as shown below:

<u>Title page,</u>
Item [56], References Cited, FOREIGN PATENT DOCUMENTS,

After "EP 0 247 777    12/1987"
Insert -- WO 96/29925  10/1996 --

After "WO 96/03074    02/1996"
Insert -- WO 92/22793  12/1992 --

Signed and Sealed this

Twentieth Day of May, 2003

JAMES E. ROGAN
*Director of the United States Patent and Trademark Office*